United States Patent [19]

Carlsson et al.

[11] 4,231,999

[45] Nov. 4, 1980

[54] METHOD IN ASSAYING METHODS INVOLVING BIOSPECIFIC AFFINITY REACTIONS AND REAGENT FOR USE IN SAID METHOD

[75] Inventors: Jan P. E. Carlsson, Uppsala; Rolf E. A. V. Axén, Bälinge; Håkan N. Y. Drevin, Brunna, all of Sweden

[73] Assignee: Pharmacia Diagnostics AB, Uppsala, Sweden

[21] Appl. No.: 882,678

[22] Filed: Mar. 2, 1978

[51] Int. Cl.$^2$ .................... G01N 33/16; A61K 43/00
[52] U.S. Cl. ........................ 424/1; 23/230 B; 435/7; 424/12
[58] Field of Search ............ 424/1, 12; 73/230 B; 195/103

[56] References Cited

U.S. PATENT DOCUMENTS

| | | | |
|---|---|---|---|
| 3,896,217 | 7/1975 | Johnson | 23/230 B |
| 4,041,146 | 8/1977 | Giaever | 424/1 |
| 4,108,975 | 8/1978 | Hales | 424/1 |
| 4,108,976 | 8/1978 | Reese | 424/1 |

*Primary Examiner*—Benjamin R. Padgett
*Assistant Examiner*—Christine M. Nucker
*Attorney, Agent, or Firm*—Fred Philpitt

[57] ABSTRACT

A method of carrying out assaying methods involving biospecific affinity reactions in which there is used a component (I), which is labelled with at least one analytically indicatable group and is soluble in the liquid in whose presence the biospecific affinity reaction is carried out, for reaction with a counterpart (II) which exhibits biospecific affinity to (I) and optionally also one or more additional counterparts exhibiting biospecific affinity to (I) and/or (II), and forming an insoluble conjugate in which the labelled component (I) is incorporated and which conjugate is separated from the liquid phase, whereafter the analytically indicatable group is assayed in the insoluble conjugate, said method being characterized in that the analytically indicatable group is bound to the component (I) with a splittable bond of covalent nature and/or one of said counterparts is bound to a carrier, which is insoluble in said liquid, with a splittable bond of covalent nature, said splittable bonds being splittable under conditions which have practically disturbing influence on the assay method used; and in that the insoluble conjugate is split at said splittable bond or bonds, in the presence of a liquid, to form fragments which are soluble in said liquid and which contain the analytically indicatable group, which group is then assayed in the liquid phase.

20 Claims, No Drawings

METHOD IN ASSAYING METHODS INVOLVING BIOSPECIFIC AFFINITY REACTIONS AND REAGENT FOR USE IN SAID METHOD

The present invention relates to a method in assaying methods involving biospecific affinity reactions, preferably immunochemical reactions, in which there is used a component (I), preferably an immunochemical component (I), which is labelled with at least one analytically indicatable group and which is soluble in the liquid in whose presence the biospecific affinity reaction is carried out, for reaction with a counterpart (II) which exhibits biospecific affinity to (I), preferably an immunochemical counterpart (II), and optionally also one or more additional counterparts which exhibit biospecific affinity to (I) and/or (II), preferably immunochemical counterparts, and forming an insoluble conjugate in which the labelled component (I) is incorporated and which conjugate is separated from the liquid phase, whereafter the analytically indicatable group is assayed in the insoluble conjugate. The invention also relates to a reagent for use in said method.

By "immunochemical component" and "immunochemical counterpart" is meant in this connection immunoglobulins (including modified immunoglobulins, e.g. aggregated, and fragments, e.g. Fabor Fc-fragments), preferably antibodies, and antigens and haptens.

Examples of components (I) and counterparts (II) which exhibit biospecificaffinity to one another are antigens (or haptens) and specific antibodies directed thereagainst. Other examples include (a) Protein A (from S. aureus) and fragments thereof, which can bind the Fc-part of immunoglobulins belonging to the IgG-class; (b) C1q, which can, for example, bind to heat aggregated IgG. (c) Lectins (e.g. Concanavalin A) which, e.g. can bond to specific carbohydrate structures in for example, biopolymers. (d) Enzyme inhibitors which can bind to their enzyme, (e) Physiologically or pharmaceutically active substances capable of binding to corresponding receptors. (f) Virus, particularly bacteriophages, able to bind cell-wall substances. There are many other such examples of pairs of substances which exhibit biospecific affinity to one another within the biochemical field.

The statement as to the labelled component (I) being soluble in the liquid in whose presence the biospecific affinity reaction is carried out (i.e. generally in water or in an aqueoues liquid) includes here and in the claims that it, for instance, may be colloidally dispersible in said liquid or in another way be present in the form of particles sufficiently small to keep themselves suspended in the liquid.

A large number of assay methods of the aforementioned basic type, primarily concerning immunochemical assay methods, are known to the art. According to one group of such methods, there is used water-insoluble polymer material to which is bound an antibody or an antigen, for example a polypeptide-containing antigen or some other counterpart. Thus, it is known from, for example. Swedish Pat. Nos. 343,949 and 341,239, and Biochem. Biophys. Acta 130 (1966) page 257, and Radioimmunoassay Methods (Editors: K. E. Kirkham and W. M. Hunter, Churchil Livingstone, London 1971) e.g. pages 405-412 of the article "Solid Phase Antigen Antibody Systems" by L. Wide, to use a water-insoluble polymer material to which an antibody or an antigen is bound by bonds of a covalent nature. Further, the U.S. Pat. No. 3,645,346 teaches an immunochemical assay method in which there is used antibodies adsorbed on the inner surface of a plastics test tube.

A further example of forming an insoluble immunochemical conjugate in this connection, is the so-called double-antibody method.

In one type of these immunochemical assay methods, an antibody bound to the polymer material is directed against an antigen which is involved in the assay method and which is immunochemically bound to the antibody on the polymer material. The antigen bound to the antibody may, in turn, possibly be reactive with an antibody in solution. In accordance with another type of these methods, an antigen bound to the polymer material is caused to react with an antibody directed against the antigen, or the antigen was been reacted with such an antibody, which in turn can be reacted with, e.g. an antigen in solution.

It is also known, when carrying out the immunochemical assay methods in question, that preferably one of the components involved in the assay method and not directly bound to the polymer is labelled with an analytically indicatable atom or group, e.g. with a radioactive atom or group, a fluorescent, luminescent or chromophoric group, or an enzymatically active group.

A large number of variants of such assay methods (including analogous methods utilizing other components (I) and counterparts (II) having biospecific affinity to each other than only immunochemical components and counterparts) in which there is used a labelled component such as a labelled antigen, a labelled hapten, a labelled antibody or labelled protein A, are found described in the literature. (See for example the aforementioned references.) In this respect, for example (a) polymer-bound antibodies can be reacted with the antigen in the sample and with labelled antigen or (b) polymer-bound antibodies can be reacted with the antigen in the sample in a manner such that the antigen is bound to the polymer-bound antibody, whereafter there is added labelled antibodies which bind to the bound antigen, or (c) the polymer-bound antigen is reacted with antibody in the sample in a manner such that the antibody binds to the antigen, whereafter there is added labelled antigen which bind to the bound antibody, or (d) the polymer-bound antigen is reacted with the antibody in the sample in a manner such that the antibody binds to the antigen, whereafter there are added labelled antibodies directed against the first-mentioned antibodies and binding thereto. The polymer-bound antibodies may also be bound over antigen to the polymer and the polymer-bound antigens may also be bound over antibodies to the polymer. The antibodies may belong to one or more immunoglobulin classes. What has been said concerning assay methods involving antigens and antibodies also applies to analogous assay methods involving other components (I) and counterparts (II).

It is also well known that such assays are preferably carried out in the presence of an aqueous liquid, e.g. a buffer solution having a suitable pH and ion strength.

In order to label the component (I), e.g. the antigen, antibody etc. with an analytically indicatable group, it is possible to chemically couple together the antigen, antibody etc. directly with the labelled group or to introduce a bridge therebetween. In order to obtain this chemical reaction there may be used, for example, amino groups in the one reactant and carboxyl groups in the other, or amino groups may be used in both of the reactants. When coupling together (conjugating) with the aid of a bridge, it is known, for example, to use such reagents as glutardialdehyde, cyanogen bromide and carbodiimides. The covalent bonds thus formed between the antigen, the antibodies or some other component (I) and the analytically indicatable group is of a permanent nature, i.e. they are not intended to be split.

When insoluble carriers are used to which an antibody, an antigen or some other counterpart is bound by means of covalent bonds, the bonds have also been of a permanent nature. In this case, the carrier is first activated by introducing reactive groups, whereafter the activated carrier is reacted with the antibody, the antigen etc. Not all of the reactive groups can be expected to establish bonds with the antibody, the antigen etc., and despite subsequent treatment for converting residual reactive groups to more inert groups, the residual reactive groups are a probable reason for the non-specific binding of components, e.g. antigens and antibodies, in a sample and also of the labelled component direct to the carrier, which have been observed with this type of determination method. Since a labelled component, in addition to being bound non-specifically itself, is able to react in biospecific affinity reactions with non-specifically bound components and the thus non-specific bound components can not be washed from the carrier, the measuring results can be considerably distorted, especially when the component to be assayed is present in very small concentrations.

In accordance with the invention there is now provided a method in which, inter alia, the aforementioned disturbances from unspecifically bound components with biospecific affinity can be reduced.

The method according to the invention is characterized by the fact that the analytically indicatable group is bound to the component (I) with a splittable bond of covalent nature and/or one of said counterparts is bound to a carrier which is insoluble in said liquid with a splittable bond of covalent nature, said splittable bonds, which may be the same or different, are splittable under conditions which have practically no disturbing influence on the assay method used, and by the fact that the insoluble conjugate in the presence of a liquid is split at said splittable bond or bonds to form fragments which are soluble in said liquid and which contain the analytically indicatable group, which is then assayed in the liquid phase.

By "conditions which have practically no disturbing influence on the assay method used" is meant, for example, conditions which do not result in considerable reduction of the activity of the analytically indicatable group, and conditions which do not damage the reagent with which the analytically indicatable group is reacted during the assay procedure, or other parts of the measuring system used.

The reagent according to the invention is characterized in that it comprises a labelled immunochemical component, comprising a multi-conjugate of a plurality of analytically indicatable groups linked together via linkages containing splittable covalent bonds, said multi-conjugate of indicatable groups in turn being bound to the immunochemical component, preferably with linkages containing splittable bonds. Preferably the splittable bonds comprise disulphide bridges —S—S—.

A particular advantage afforded by the method according to the invention is that radiation-absorbing effects from the solid conjugate can be avoided, which is particularly advantageous when, for example, a fluorescent group or a luminescent, chromophoric or radioactive group, e.g. a $\beta$-radiating group is used as the analytically indicatable group.

In this respect it is particularly preferred to split the bond between the analytically indicatable group and component (I) rather than split between the carrier and the counterpart bound thereto, since in the former case radiation-absorbing effects from other conjugate participants can be avoided.

Corresponding circumstances also apply when the analytically indicatable group is an enzymatically active group. Thus, enzymes which are conjugated as analytically indicatable groups to some other macromolecular often exhibit lower activity than the corresponding native enzyme. This reduction in activity is due to the fact that the enzyme, as a result of conjugation, is sterically prevented from acting on its substrate. A further reason may be the diffusion control which often occurs in the water layer nearest the enzyme conjugate. By releasing the enzyme label, the activity can be measured in the liquid phase, whereby optimal enzyme activity is obtained. This also enables the use of water-insoluble substrates for the enzyme assay. Thus, according to the invention not only enzymes (e.g. hydrolases, oxidases, reductases etc.) previously used as labelling substances in immunochemical assay methods can be used as the labelling substance but also enzymes working on high molecular weight substrates, even insoluble substrates, can be used. Preferably, the enzymatically active group is the only part in the conjugate which is bound with a splittable bond according to the invention.

The method also affords advantages from the aspect of measurement technique, since the labelled substance can be transferred between vessels in liquid phase, instead of in the less readily handled solid form, which facilitates automation of the analysis. Preferably the liquid phase used when splitting is an aqueous liquid, e.g. a buffer solution, of suitable pH and ion strength.

In the majority of cases the embodiment of the invention most preferred is that variant in which only the bond between the component (I) and the analytically indicatable group shall be splittable, and in which said bond is split in conjunction with the assay.

The embodiment involving a splittable bond between a counterpart and an insoluble carrier is of particular value in such cases when disturbing unspecific adsorption of labelled component (I) of the solid phase takes place. The splittable bond may in this case be the only splittable bond but it is to particular advantage in many cases that also the bond between component (I) and the indicatable group or groups is splittable, in which case suitably another type of splittable bond is chosen than that between the counterpart and the insoluble carrier whereby the particular advantage is obtained that the two splittings can be carried out in two different steps.

The splittable bonds may, for example, be split by reduction, oxidation, hydrolysis or exchange reactions. An advantageous bond in this connection is the bridge —S—S—, which can be split by, for example, reduction or thiol disulphide exchange. A further advantageous bond in this connection is one containing a vicinal diol-structures, which can be split oxidatively with sodium periodate. Examples of hydrolytically splittable bonds are ester bonds and glycosidic bonds. If suitable, splitting of the bond can be facilitated by means of a catalyst, e.g. an enzyme, such as an esterase or a glycosidase.

An —S—S— bridge can be established by introducing one or more thiol groups (if not already present) in one of the two substances to be coupled together, and one or more disulphide structures activated for thiol disulphide exchange in the other molecule, i.e. if for example a thiol group is introduced into the labelling substance, the substance exhibiting biospecific activity and shall be coupled together with the labelling substance, should be provided with disulphide structure, and vice versa. The two modified substance types are then caused to contact each other, said substances being bound together with —S—S—bonds via a thiol disulphide exchange reaction.

Preferably there is found on both sides of the —S—S—bridge a carbon atom which may form part of an aliphatic or aromatic group. The said carbon atoms are, in turn, preferably bound to at least one carbon atom. Remaining bonds of the first-mentioned carbon atoms are preferably saturated with hydrogen atoms. Each of the first-mentioned carbon atoms may, for example, be included in the group —CH$_2$— and/or

where the carbon atom is seated in an aromatic ring, such as a benzene ring. Consequently, the disulphide bridge is preferably seated in a group of the formula

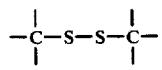

where one of the remaining bonds of each of said carbon atoms passes to another carbon atom and remaining bonds of each carbon atom pass to hydrogen and/or carbon.

For the introduction of the thiol groups there can be used known thiolating agents, such as thiolimidate of the formula

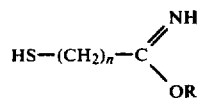

where R is methyl or ethyl and n is an integer from 1-10, preferably from 2-4, or N-acetylhomocystein thiolactone.

The reaction is carried out in aqueous solution in a slightly alkaline environment (pH 7-9) and a temperature of 15°-30° C. with a high surplus of thiolating agent.

For the purpose of introducing a disulphide structure activated for thiol disulphide exchange, there can for example be used known disulphides whose corresponding reduced from is of low S-nucleophilicity depending on resonance stabilization or thiolthion-tautomerism and which are to be reacted with thiol group-containing substances. Examples of such disulphides are 2,2'-dipyridyl-disulphide, 4,4'-dipyridyl-disulphide and corresponding compounds substituted in the pyridyl group, in which compounds the substituents are of such type and in such position that the thiolthion-tautomerism is not disturbed, for example such having a nitro- or carboxyl group in the 5-position.

The reaction of the thiol-containing substance with the disulphide of the mentioned type is carried out in aqueous solution at pH 2-9 and a temperature of 15°-30° C. with a high disulphide surplus.

Preferably there is used, however, for both thiolation and introduction of activated disulphide structure a heterobifunctional reagent of the formula

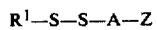

R$^1$—S—S—A—Z    I where R$^1$ is 2-pyridyl, 5-nitro-2-pyridyl or 4-pyridyl, A is a hydrocarbon residue having from 1-10 carbon atoms, preferably from 1-6 carbon atoms, and Z is a group

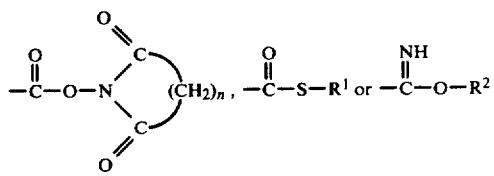

or acid addition salts of the last mentioned group, where n is 2 or 3, R$^1$ has the same significance as R$^1$ above and is equal thereto and R$^2$ is methyl or ethyl.

The compounds of formula I can be prepared in a number of different ways. The methods preferred today are the following:

Compounds of the formula I, in which Z is the group

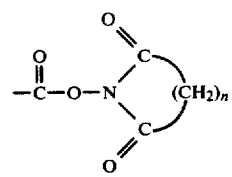

are prepared by reacting a disulphide of the formula

R$^1$—S—S—A—COOH    (II)

where R$^1$ and A both have the above significance, with N-hydroxysuccinimide when n=2 (or the analogous compound with n=3 when compounds with n=3 are desired) in the presence of a condensing agent.

The reaction is carried out in an organic solvent at a temperature of 10°-30° C. A suitable solvent is, for example, methylene chloride, ethylene acetate and dioxane. The reaction time varies with the choice of reaction components and reaction temperature.

The condensating agent used may be one which is commonly used in esterifying reactions, such as N,N'-dicyclohexylcarbodiimide.

The starting compound of the formula II can be prepared by reacting a mercaptoalkyl carboxylic acid of the formula

HS—A—COOH    (III)

with a dipyridyl disulphide of the formula

R$^1$—S—S—R$^1$    (IV)

in which formulae A and R$^1$ both have the aforestated significance.

This reaction is carried out in an organic solvent at a temperature of 10°-30° C. A suitable solvent is, for example, ethanol, ethyl acetate and dioxane. The reaction time varies with the selection of reaction components and the reaction temperature.

Compounds of the formula I, in which Z is the group

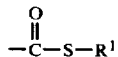

are prepared by reacting a disulphide of formula II above with a corresponding thiopyridone in the presence of a condensing agent in an organic solvent at an initially low temperature, for example −20° C., for approximately 1-2 h, and thereafter at ambient temperature (e.g. 20° C.). A suitable solvent in this respect, is for example, methylene chloride, ethyl acetate and dioxane. The condensating agent used is preferably N,N'-dicyclohexylcarbodiimide.

The starting material used is preferably a mixture obtained by reacting a compound of formula III with a compound of formula IV.

Compounds of the formula I, in which Z is the group

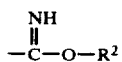

are prepared by reacting a thiolimidate of the formula

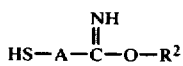

in which $R^2$ and A both have the aforementioned significance, with a pyridyl disulphide of the formula $R^1$—S—S—$R^1$, in which $R^1$ has the above significance, in an organic solvent. The solvent, for example, may be methanol containing approximately 10% glacial acetic acid.

The use of these reactants can be illustrated by the following list of reactions, in which N-succinimidyl-3(2-pyridyldithio)propionate has been chosen as an example of a suitable bifunctional reactant:

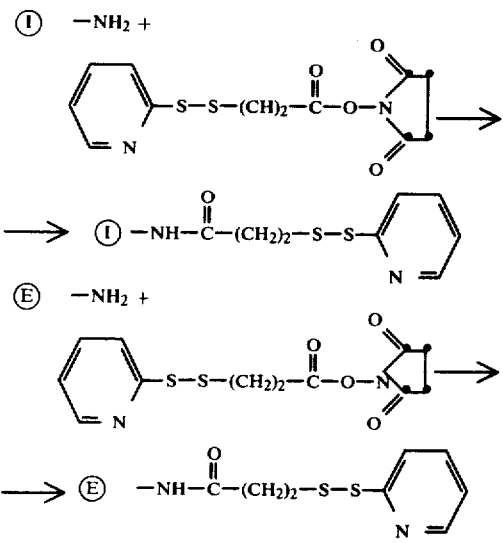

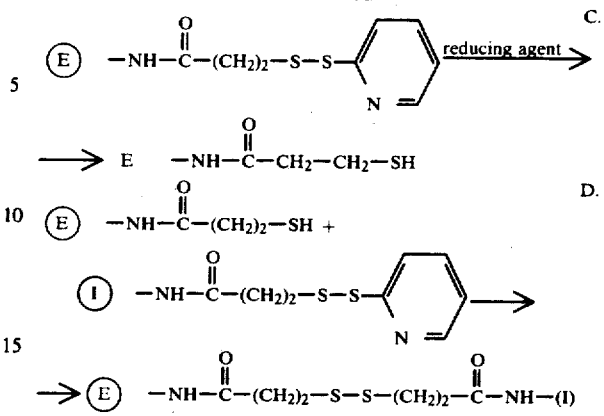

In the above formulae,(I)—NH₂ gives an example of an immunochemical reactive component (I) or some other component (I) having biospecific affinity to a counterpart (II) and(E)—NH₂ indicates an example of an indicatable group, e.g. an enzyme or a group containing one or more radioactive atoms. In the reduction in step C above it is possible to use DTT (Dithiothreitol). It is possible with this reducing agent to reduce, e.g., protein-bound pyridyl disulphide structure without, at the same time, reducing native disulphide bridges which may occur in the protein. This is achieved by carrying out the reduction at a pH ~3-5 with a surplus of DTT or at a higher pH with a smaller surplus or equimolar quantities of DTT.

The degree of substitution of thiol or disulphide groups in for example a protein can be relatively easily controlled in this derivatisation method (formula B above) by varying the molar surplus of reagent or by varying the pH between the range 5-8.

For example, bimolecular conjugates containing, e.g. one enzyme molecule (as the indicatable group) and one other protein-molecule having biospecific affinity (e.g. an antibody) can be prepared by introducing one thiol group and one disulphide structure in respective molecules and causing the modified molecules to react by means of thiol disulphide exchange. Since the thiol disulphide exchange reaction requires a thiol and a reactive disulphide structure and only one of these groups is found in each molecule, conjugates comprising only one type of molecule can be avoided. Oligomolecular or polymolecular conjugates can be obtained in a similar manner.

It is to particular advantage to choose, as the indicatable group, an enzyme which contains at least one native HS-group which is made use of for the formation of a splittable disulphide bridge, because derivatisation can be avoided in this case and the enzyme be obtained in its native form with full activity after reduction of the disulphide bridge.

Naturally there can be obtained in a similar manner other labelled components (I) with other indicatable groups with a splittable bond between the indicatable group and the component (I). Also, counterparts can be bound to an insoluble carrier via a splittable bond using similar methods.

The aforementioned thiol disulphide exchange reactions can be carried out in an aqueous environment at a pH of from 2-8 and a temperature of from 15°-30° C.

In certain instances, it may be desirable to avoid a direct conjugation of the analytically indicatable group to components having biospecific affinity. For example, the two types of molecule may act deleteriously on each other's activity, by, for example, hydrophobic interaction and/or effects of charges. In such cases it may be suitable to use a soluble carrier for both the analytically indicatable group and the component (I) having biospecific affinity, which group and component are then each coupled to said soluble carrier with bridges of the aforementioned type comprising or containing the group —S—S—, whereby they are separated from each other. The sensitivity of a test based on such conjugates can be increased by attaching a large number of analytically indicatable groups to a soluble carrier to which there is also coupled only one or a few molecules of the component (I) having biospecific affinity.

The aforementioned soluble carrier may be, for example, dextran, a dextran derivative, biopolymers which are inert in the system and other polymers which are soluble in the liquid in whose presence the biospecific affinity reaction is carried out. (In this instance a bond in the soluble carrier may constitute a splittable bond, e.g. a glycosidic bond, which can be split by a glycosidase, e.g. dextranase, when the soluble carrier comprises dextran.)

The coupling is effected, for example, by introducing disulphide structures into the carrier and HS-groups into the label and into the component (I), which are then coupled to the polymer by a thiol disulphide exchange reaction. For the purpose of coupling either the component (I) or the label to the water-soluble carrier there may also be applied other methods known for coupling such substances to carriers, since it is not necessary for both of these substances to be splittable from the water-soluble carrier.

The disulphide bridge —S—S— can be readily split off under mild conditions with the aid of, for example, DTT as a reducing agent, in such a manner that the indicatable group is released in a liquid phase and there can be assayed, and hence the bridge —S—S— is particularly suitable as a splittable bond.

When a particularly high sensitivity is wanted in the analysis, there may according to a valuable embodiment of the invention be used a labelled component (I) comprising a multiconjugate of a plurality of analytically indicatable groups linked together via linkages containing splittable covalent bonds (for instance disulphide bridges —S—S—), said multiconjugate of indicatable groups in turn being bound to the component (I), preferably with linkages containing splittable bonds (for instance disulphide bridges —S—S—).

Bonds containing vicinal diol structures

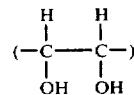

can be obtained, for example, with the aid of bifunctional agents of the type

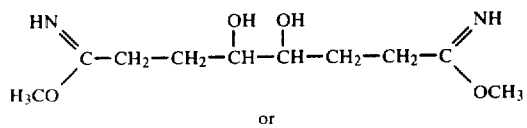

or

-continued

CH₂——CH—CH——CH₂
   \  /      \  /
    O         O

Bonds containing enzymatically splittable glycoside bonds can be obtained, for example, by joining the analytically indicatable group or groups with the component (I) via a glycoside, an oligosaccharide, or a polysaccharide chain, e.g. a dextran chain or a starch chain, which is splittable with dextranase or amylase.

When one of the components taking part in the affinity reaction is bound to a carrier which is insoluble in the liquid in whose presence said reactions are carried out, the carrier may, in principle, comprise any such carrier material known in conjunction with previously known methods of the type mentioned in the introduction. Examples of such carrier materials are insoluble organic or partly inorganic polymers such as cellulose, crosslinked dextran, agarose, cross-linked polyacrylamide, cross-linked polystrene and glass derivatives. When it is considered that the bond between this carrier and the component bound thereto is not to be split in accordance with the invention, the bond may be a conventional bond, i,e, it may comprise a bond of covalent nature of conventional type, or a so-called hydrophobic bond.

In a corresponding manner, the bond between the analytically indicatable group and the component (I) may be a conventional bond when there exists a splittable bond according to the invention between a counterpart and a solid carrier and when it is not considered necessary to split the firstmentioned bond.

The invention will now be described in more detail with reference to a number of examples.

EXAMPLE 1

Quantitative assay of Salmonella-antibodies in human serum with rabbit-antihuman
Fc-γ-α-amylase-conjugate (a) Preparation of rabbit-antihuman Fcγ-α-amylase-conjugate α-amylase (bacterial type IIA, Sigma, USA) purified by ion-exchange chromatography on DEAE-Sephadex ® (beads of diethylaminoethyl-containing dextran cross-linked with epichlorohydrin from Pharmacia Fine Chemicals AB, Uppsala, Sweden) was dissolved in 2 ml of 0.1 M Na-phosphate buffer. 0.7 ml of N-succinimidyl-3(2-pyridyldithio)propionate (11 mM in 99.5% EtOH) was added to the solution. The reaction was permitted to continue (after being shaken) for 60 minutes at −23° C. Surplus reagents and other undesirable low-molecular weight components were then removed by gel filtration on Sephadex ® G/25 (beads of dextran cross-linked with epichlorohydrin from Pharmacia Fine Chemicals AB, Uppsala, Sweden) (medium used was the same phosphate buffer as above).

4.8 mg of rabbit-antihuman Fcγ-antibodies (prepared from rabbit serum by immunosorption purification) in 2.5 ml of 0.1 M Na-phosphate buffer at pH 7.5 were reacted with 13 μl of N-succinimidyl-3(2-pyridyldithio)propionate (11 mM in 99.5% EtOH) at +23° C. for 60 minutes. Surplus reagent was removed by gel filtration on Sephadex ® G-25 (the medium used was 0.1 M Na-acetate 0.3 M NaCl, pH 5.0). The void material containing the modified antibodies was reduced with 0.2 ml of 50 mM dithiothreitol (DTT) (pH 5.0) for 20 minutes.

Surplus DTT was removed by gel filtration on Sephadex ® G-25 (the medium used was 0.3 M NaCl).

The thus thiolated antibodies, approximately 2.1 mg in 3 ml of 0.3 M NaCl, were mixed with α-amylase-2-pyridyl disulphide derivative (approx. 10 mg in 1.5 ml of 0.1 M Na-phosphate-0.3 M NaCl pH 7.5) prepared in the aforedescribed manner. The reaction was permitted to continue for 48 hours at +4° C., whereafter undesirable low molecular weight components were removed by gel filtration on Sephadex ® G-25 (the medium used was 0.3 M NaCl).

N-succinimidyl-3(2-pyridyldithio)propionate can be prepared in the following manner:

1.9 g (8.5 mmole) 2,2'-dipyridyl disulphide is dissolved in 10 ml of ethyl acetate. A solution of 0.9 g (8.6 mmole) 3-mercaptopropionic acid in 10 ml ethyl acetate is added dropwise for 15 minutes whilst stirring, at the same time as 0.5 mg (2 drops) boron trifluoride etherate is added to the reaction mixture. After 20 h at room temperature under agitation, the reaction mixture is vaporized (Büchi Rotavapor, <40° C.) and the solid yellow residue is slurried in 10 ml (cold) (+4° C.) ethyl acetate and filtered. 0.68 g (5 mmole) of N-hydroxysuccinimide are added to the filtrate, whereafter 1.03 g (5 mmole) of dicyclohexylcarbodiimide dissolved in 10 ml dry ethyl acetate are added dropwise for 15 minutes whilst stirring at room temperature. The reaction is permitted to continue under agitation for 5 h at room temperature, whilst the reaction mixture is cooled to +4° C. and the precipitated dicyclohexylcarbamide is filtered off. The slightly yellow solution is vaporized and the oil dissolved in ethanol and permitted to crystallize at −20° C. The yield is 45% and the melting point will be found to be 78.5°-80.5° C.

(b) Quantitative assay of Salmonella-antibodies in human serum with rabbit-antihuman Fcγ-α-amylase-conjugate Salmonella O-antigen of type D (9.12) was diluted in cold 0.1 M sodium carbonate buffer, pH 9.6 with 0.02% $NaN_3$ to 5 μg/ml. 1 ml antigen solution was poured into disposable polystyrene tubes. The tubes were incubated at +4° C. for 16 h.

Human serum (a series with serum taken from a patient who was infected with Salmonella bacteria of sero type DO and a series with human normal serum (HNS) was diluted with PBS (0.015 M Na-phosphate, pH 7.2, 0.05% Tween ® 20 Tween ® 20: sorbitan monooleate polyoxyethylene), 0.02% $NaN_3$, 0.9% NaCl) 100 to 100 000 times. A number of tubes prepared in accordance with the above were washed with 0.9% NaCl-0.05% Tween ® 20. The tubes filled with the washing solution were permitted to stand for a minute or two and emptied with water-suction. This was repeated twice.

1 ml of diluted serum was poured into each tube (double test). These tubes were then incubated for 4 h at +23° C. During this incubation period any antibodies against the Salmonella-antigen will bind to that part of the tube wall coated with the antigen. The tubes were then washed again in order to remove all other serum components.

Added to the tubes were a conjugate prepared in accordance with (a) above diluted 100 times with PBS (1 ml to each tube). The tubes were then incubated for 16 h. Surplus conjugate was then washed away using the same washing procedure as that previously applied.

The α-amylase was released from the immunochemical complex of antigen-antibody-(antibody-enzyme-conjugate) bound to the tube wall by adding to each tube 1 ml of dithiothreitol (5 mM in PBS). Subsequent to incubation for 20 minutes at 23° C., there was added 1 ml water and a half table of Phadebas ®. Amylase test (Phadebas ® amylase test from Pharmacia Diagnostics AB, Uppsala, Sweden; water-insoluble, cross-linked blue starch in tablet form). The tubes were vigorously shaken and then permitted to stand for 1 h at 37° C., whereafter the reaction was interrupted by adding 100 μl of 5 M NaOH. After removing undissolved starch polymer by filtration, the extinction of the blue-coloured filtrate was determined at 620 nm, as a measurement of the released amylase.

The obtained extinction values are shown in Table I below:

TABLE I

| Serum | Dilution | Extinction $A_{620}/h$ |
|---|---|---|
| human anti-DO | $10^{-2}$ | 2.36 |
| " | $10^{-3}$ | 0.72 |
| " | $10^{-4}$ | 0.12 |
| " | $10^{-5}$ | 0.09 |
| HNS | $10^{-2}$ | 0.100 |
| " | $10^{-3}$ | 0.02 |

Thus the antibodies could be detected in patient serum diluted $10^5$ times. Blank-tests gave very low extinctions. Corresponding tests, in which the reductive splitting of the α-amylase from the immunocomplex adsorbed on the tube walls was excluded gave an extinction of $(A_{620}/h) \leq 0.01$.

EXAMPLE 2

A quantitative assay of Salmonella-antibodies in human serum with rabbit-antihuman Fcγ-α-amylase-conjugate Example 1 was repeated but with the exception that the enzyme activity was assayed with the use of soluble starch. In addition there was carried out a parallel test without the reductive splitting of the α-amylase.

Instead of a half tablet Phadebas ® amylase test there was added to each tube in this test, 1 ml of starch (2% in PBS). After incubation for 60 minutes at 37° C., there was added 0.5 ml of 3,5-dinitrosalicylic acid solution (prepared by dissolving 1 g of 3,5-dinitrosalicylic acid in 40 ml of NaOH + 30 ml $H_2O$ and then adding 30 g of potassium sodium tartrate and diluting the solution to 100 ml with $H_2O$). The tubes were heated for 5 minutes in a bath of boiling water and 5 ml from each tube was then transferred to tubes containing 5 ml of distilled water. The extinction of the resultant solutions was determined after 10 minutes at λ=500 nm.

The results are shown in Table II below.

TABLE II

| Serum | Dilution | Extinction $A_{500}$ (α-amylase not split) | Extinction $A_{500}$ (α-amylase split off) |
|---|---|---|---|
| Human anti DO | $10^{-2}$ | 0.032 | 0.42 |
| " | $10^{-3}$ | 0.010 | 0.13 |
| HNS | $10^{-2}$ | 0.005 | 0.006 |
| " | $10^{-3}$ | 0.006 | 0.008 |

(The extinction values were corrected with regard to the effect of dithiothreitol)

EXAMPLE 3

Assay of rabbit-antihuman serum albumin-antibodies with human serum albumin-α-amylase conjugate (a) Preparation of albumin-α-amylase conjugate 8 mg of human serum albumin in 1 ml of 0.1 M Na-phosphate buffer, pH 7.5, was admixed with 12 μl of N-succinimidyl-3(2-pyridyldithio)propionate (40 mM in 99.5% ethanol). After reacting for 40 minutes at +23° C., the reaction mixture was gel filtered on a Sephadex ® G-25 column (medium used was the same phosphate buffer as above). The void material, approx. 2 ml, contained albumin-2-pyridyl disulphide derivative. A spectrophotometric assay of the amount of 2-thiopyridone freed after reduction of the derivative showed a substitution degree of 2.5 mole thiol/mole albumin.

20 mg of α-amylase were dissolved in 1.5 ml of 0.1 M Na-phosphate buffer pH 7.5. 150 μl N-succinimidyl-3(2-pyridyldithio)propionate (40 mM in 99.5% ethanol) were added and the reaction was permitted to continue for 60 minutes at +23° C. Surplus reagent and other undesired low-molecular weight components were removed by gel filtration on Sephadex® G-25 (the medium used was the same phosphate buffer as above).

The α-amylase-2-pyridyl disulphide derivative formed (20 mg in approx. 2.5 ml) was then reduced with 10 mg of dithiothreitol at +23° C. for 20 minutes. Surplus dithiothreitol was then removed by gel filtration on Sephadex ® G-25 (the medium used was 0.3 M NaCl).

The thiolated α-amylase (~20 mg containing approximately 0.7 mole SH/mole protein) in 3.5 ml of 0.3 M NaCl was mixed with 5.6 mg albumin-2-pyridyl disulphide derivative in 1.4 ml of 0.1 M Na-phosphate buffer, pH 7.5. The reaction was permitted to continue for 18 hours at +4° C. The reaction mixture was then separated on Sephadex ® G-200 (the medium used was 0.3 M NaCl). When analysing the different fractions, α-amylase active material having a higher molecular weight than native α-amylase was found. The estimated molecular weight corresponded to oligomers comprising 1 (one) albumin molecule and 1-2 α-amylase molecules.

The fractions which contained conjugate were combined and stored in 0.3 M NaCl at +4° C. (approximately 10 mg protein/ml).

(b) Assay of rabbit-antihuman serum albumin-antibodies with human serum albumin-α-amylase conjugate 1 ml of 0.05 M Na-phosphate buffer pH 7 containing 100 μg human serum albumin (HSA)/ml was added to disposable polystyrene test tubes. The tubes were incubated at +37° C. for 3 h. The tubes were then washed with 3×2 ml buffer containing 0.05 M Na-phosphate, pH 7.4, containing 0.3% dextran, 0.9% NaCl and 0.5% Tween (PDT-buffer). Rabbit-antiHSA-serum was diluted with PDT-buffer 10–10⁴ times. 0.5 ml of each dilution was poured into a tube treated according to the above. An equal number of blank tests was prepared with 0.5 ml rabbit-normal serum (RNS) diluted in the same way. The tubes were allowed to stand for 3 h at +23° C. The tubes were then washed with 3×2 ml of the PDT-buffer and 0.5 ml of HSA-α-amylase conjugate from (a) above were added. The tubes were then incubated for 16 h at +23° C. Surplus conjugate was washed away with 3×1 ml PDT-buffer. 0.5 ml of 10 mM dithiothreitol (DTT) in 0.05 M Na-phosphate buffer, pH 7, was added to the tubes. After 15 minutes, the liquid phase in the tubes was transferred to tubes having therein 0.5 ml of distilled water containing ¼ of a tablet Phadebas ® α-amylase test. These tubes were incubated for 2 h at 37° C. after being shaken, whereafter undissolved starch substrate was centrifuged down and the extinction of the supernatant was determined at 620 nm.

The results showed that rabbit-antiHSA-antibodies with used serum could be detected in serum which was diluted $10^4$ times, while the blank tests with RNS gave $A_{620}$-values $\leq 10\%$ of the found values in the sample serum. Comparison tests with omission of the reductive splitting of the α-amylase from the immuno complex adsorbed on the tube walls gave an extinction of $(A_{620}) \leq 0.02$.

EXAMPLE 4

Assay of rabbit-antihuman serum albumin-antibodies with sheep-antirabbitIgG-antibodies-dextran-α-amylase conjugate (a) Preparation of sheep-antirabbitIgG-antibody-dextran-α-amylase conjugate 1 g of bromohydroxypropyl dextran was dissolved in 12.5 ml of distilled water and 3.8 g of $Na_2S_2O_3 \times 7\, H_2O$ were added. The reaction was permitted to continue for 3 h at 100° C. The mixture was then dialyzed against $H_2O$ (2×2 l for 24 h and 1×10 l for 6 h).

The content of the dialysis bag was freeze-dried and is hereinafter referred to as Bunte salt dextran. Analysis showed that the dextran derivative contained 2.1 mmole S/g dry derivative. 1 g of Bunte salt dextran was dissolved in 10 ml of 50% ethanol-50% 0.1 N Na-phosphate buffer, pH 8.3. 0.7 g of 2,2'-dipyridyl disulphide was added and the mixture was heated to 60° C. and maintained at this temperature for 24 h. The reaction mixture was then dialyzed against 50% ethanol 3×3 l (each dialysis for 6 h) and against distilled water 3×3 l (each dialysis for 2 h).

2.6 mg of sheep antirabbitIgG-antibodies (prepared from sheep serum by $Na_2SO_4$-precipitation) were dissolved in 1 ml of 0.1 M Na-phosphate buffer pH 7.5. 120 μl of N-succinimidyl-3(2-pyridyldithio)propionate (1.6 mM in 99.5% ethanol) were added and the reaction was permitted to continue, subsequent to shaking, at +23° C. for 30 minutes. The reaction mixture was then gel filtered on Sephadex ® G-25 (the medium used was 0.1 M Na-acetate buffer, pH 5.0). The void material (2.5 ml) (2-pyridyl disulphide sheep antirabbitIgG-antibody derivative) was reduced with 64 μl 50 mM dithiothreitol. After 15 minutes at +23° C., surplus dithiothreitol was removed by gel filtration on Sephadex ® G-25 (the medium used was 0.3 M NaCl). A void volume of 3.5 ml was obtained. 2.4 mg of thiolated α-amylase (prepared in the manner described in Example 1) (in 1.5 ml) and 2.6 mg thiolated sheep antirabbitIgG-antibodies (see above) in 3.5 ml were mixed with 1.6 mg of 2-pyridyl disulphide dextran in 1 ml of 0.1 M Na-phosphate buffer, at pH 7.5. Subsequent to shaking, the mixture was allowed to stand for 10 minutes and then gel filtered on Sepharose ® 6B (beads of agarose from Pharmacia Fine Chemicals AB, Uppsala, Sweden) with 0.3 M NaCl was the medium. Fractions containing conjugates were combined.

(b) Assay of rabbit-antihuman serum albumin-antibodies with sheep-antirabbitIgG-antibody-dextran-α-amylase conjugate 50 discs of nylon net (diameter 8 mm, weight 1.5 mg/each) were partially hydrolyzed in 50 ml of 3 M HCl for 30 minutes at 23° C., and then activated with 0.1% glutardialdehyde in accordance with L Lyle et al., J. Immunol., vol. 113 (1974) 517. The activated nylon nets were washed with 0.05 M Na-phosphate buffer, pH 7, and then transferred to 20 ml of 0.9% NaCl containing human serum albumin (HSA) (0.5 mg/ml). After 60 minutes at 23° C. the nonimmobilized HSA was washed with 0.9% NaCl and the nylon nets with bound HSA were treated with 50 ml of $NaBH_4$ (0.4 mg/ml) at 23° C. for 30 minutes, there being formed stable covalent bonds between HSA and the nylon matrix. The nylon discs were finally washed with a PDT-buffer. Rabbit-antiHSA-serum was diluted in the PDT-buffer 10–$10^4$ times. 200 μl of each dilution was incubated with 1 nylon disc in a test tube at 23° C. for 3 h. An equal number of blank tests were prepared with 200 μl of rabbit normal serum (RNS) diluted in the same manner. The nylon discs were then washed with 3×2 ml PDT-buffer.

The antibody-dextran-α-amylase conjugate from (a) above was diluted ten times and 20 μl of the thus obtained solution was incubated with nylon discs (prepared in accordance with the above) for 16 h at 23° C. Surplus conjugate was removed by decanting and the nylon nets were washed with 3×2 ml PDT-buffer.

The α-amylase activity (with and without splitting the α-amylase) was determined in a manner analogous with that described in Example 1.

With the serum used it was possible to observe rabbit-antihuman serum albumin-antibodies in the dilution range 10–$10^4$ times. Blank tests with RNS gave α-amylase activities of ≦10% of the measuring values obtained with corresponding dilutions within said range.

EXAMPLE 5

Assay of rabbit-antihuman serum albumin-antibodies with human serum albumin-glutathione-fluorescein conjugate (a) Preparation of albumin-glutathione-fluorescein conjugate 100 mg of fluorescein isothiocyanate were reacted with 35 mg of oxidized glutathione in 4 ml of distilled water. The reaction was permitted to continue at constant pH-value (pH 9) for 90 minutes. The reaction mixture was gel filtered on a 100 ml Sephadex ® G-25 column (the medium used was 0.3 M NaCl). The fractions corresponding to the total volume were slurried (10.3 ml with A493=41.2). The pH was adjusted to 9 with a Na-borate buffer. The solution was then pumped through a column containing 2.2 ml mercaptohydroxypropylagarose (prepared from beads of agarose (Sepharose ® 6B from Pharmacia Fine Chemicals AB, Uppsala, Sweden) in accordance with Axen et al., Acta Chem. Scand. B 29 (1975) 471–474; gel containing 660 μmole SH/g dried gel was used) equilibrated with 0.1 M Na-borate buffer, pH 9. The flow was 10 ml/h. The eluate was slurried in 1 M Na-acetate pH 4, and its fluorescein and thiol content was determined. In the following test there was used a fraction (3 ml) having a thiol concentration of 1.19 mM and a fluorescein concentration of 0.60 mM.

20 mg of human serum albumin dissolved in 1 ml of 0.1 M Na-phosphate buffer, pH 7.5. 150 μl of 40 mM N-succinimidyl-3-(2-pyridyldithio)propionate (in 99.5% ethanol) were added. Subsequent to being shaken, the mixture was permitted to stand for 40 minutes at +23° C. Surplus reagent was then removed by gel filtration on Sephadex ® G-25 (the medium used was 0.1 M Na-phosphate buffer pH 7.5). 3 ml of the void material (19 mg of 2-pyridyl disulphide albumin) were mixed with 3 ml of glutathionefluorescein. The mixture was permitted to stand for 30 minutes at room temperature and was then gel filtrated on Sephadex ® G-25 with 0.9% NaCl as the medium. Analysis showed that the void (9 ml) contained 17.1 mg of albumin with approx. 3.5 mmole fluorescein/mole albumin.

(b) Assay of rabbit-antihuman serum albumin-antibodies with human serum albumin-glutathione-fluorescein conjugate Coating of the tube walls with HSA and incubation with rabbit-antiHSA-serum was carried out in a manner analogous with that described in Example 3.

To the thus obtained tubes there was added 0.5 ml of a conjugate (1.9 ml conjugate/ml) prepared in accordance with (a). The tubes were incubated for 16 h at 23° C., whereafter surplus conjugate was decanted and washed away with 3×2 ml PDT-buffer.

1 ml of dithiothreitol (25 mM in distilled water, pH 7) was added to the tubes. After 15 minutes the liquid phase was transferred to cuvettes for fluorimetric measurements and the fluorescence intensity was determined with 473 nm as wavelength for excitation and 530 nm as emitting wavelength.

With the serum used it was possible to detect fluorescence in the serum dilution range of 1–50 times. With RNS the fluorescence intensities obtained were ≦10% of respective corresponding test values.

Because of the manner in which the test was carried out (i.e. with binding to the tube walls) it was, of course, not possible to carry out the measurement without splitting the fluorescent labels. Fluorescence measurements carried out on solely the conjugate showed, however, that a considerably higher fluorescence intensity is obtained after splitting the conjugate.

EXAMPLE 6

Assay of dog-serum albumin specific IgE with Sephadex ® dog serum albumin conjugate and $^{125}$I-labelled rabbit-antihumanIgE-antibodies (a) Preparation of Sephadex ®-dog serum albumin conjugate 36 g of Sephadex ® G-15 (beads of dextran cross-linked with epichlorohydrin from Pharmacia Fine Chemicals AB, Uppsala, Sweden) were suspended in 200 ml of 0.5 M NaOH. 17 ml of 1-chloro-2,3-epoxypropane were added dropwise for 5 minutes at 23° C. The temperature was then raised to 60° C. and the reaction was permitted to continue for 2 h. The product was then washed with water snf 0.5 M Na-phosphate buffer, pH 6.5, and suspended in 200 ml of said buffer. 100 g of $Na_2S_2O_3 \times 7$ $H_2O$ were added and the reaction was permitted to take place for 2 h, whereafter the product was washed with water on a Büchner funnel. The product was treated with 2.8 g of dithiothreitol (DTT) in 0.1 M $NaHCO_3$, pH 8.3, 200 ml total volume. After reacting for 60 minutes, the product was washed with 1 mM acetic acid and thereafter 0.05 M $NaHCO_3$-1 mM EDTA containing 50% acetone. The product was suspended in 40 ml of the last-mentioned solution, in which there was dissolved 2,2'-dipyridyl disulphide to a concentration of 0.15 M. The reaction was permitted to continue for 60 minutes at 23° C. 600 ml of water were then added and the reaction was allowed to continue for a further 60 minutes, whereafter the product was washed with water and shrunk with acetone and dried over a blue gel. The thus obtained product was found to contain approx. 40 μmole 2-pyridyl disulphide structures per gram of dry derivative.

20 mg of dog serum albumin were dissolved in 2 ml of 0.1 M Na-phosphate buffer, pH 7.5, which was 25 mM with regard to mercaptoethanol. After 60 minutes surplus mercaptoethanol was removed by gel filtration on Sephadex ® G-25 (the medium used was 0.1 M Na-phosphate buffer, pH 7.5).

1 g of Sephadex ®-derivative (see above) was swollen and washed in 0.1 M Na-phosphate buffer, pH 7.5 and then suspended in 2 ml of said buffer. Albumin (3.5 ml) treated in accordance with the above was added to the suspension. The reaction was carried out under agitation by rotating the suspension in a closed vessel for 36 h at 23° C. The thus obtained Sephadex ®-albumin conjugate was then washed on a glass filter funnel with 0.1 M Na-acetate-0.3 M NaCl, pH 5.0 and then suspended in 10 ml of said solution, whereafter 40 mg of glutathione were added to eliminate non-reacted pyridyl disulphide structures. After 3 h reaction at 23° C., the product was washed with 0.9% NaCl and stored in the form of a suspension in 0.9% NaCl.

(b) Assay of dog serum albumin specific IgE with Sephadex ®-dog serum albumin conjugate and $^{125}$I-labelled rabbit-antihumanIgE-antibodies The suspension from (a) was centrifuged and the supernatant removed by suction. Sephadex ®-albumin conjugate was washed with 10 ml PDT-buffer and resuspended in 10 ml PDT-buffer. 200 μl of the suspension were charged to Ellerman-tubes. The volume was adjusted to 400 μl with PDT-buffer, whereafter 100 μl of human serum containing specific IgE against dog serum albumin were added. The thus obtained suspension was incubated under rotation for 3 h at 23° C. After being washed three times with centrifugation, removal by suction and addition of PDT, there was added $^{125}$I-antiLgE (15 ng. 94200 cpm, Phadebas ® RAST isotope reagent, Pharmacia Diagnostics AB, Uppsala, Sweden). The tubes were incubated over night at 23° C. After being washed three times in the aforedescribed manner, the radioactivity bound to the Sephadex ®-conjugate was assayed in a conventional manner with a γ-counter. The $^{125}$I-containing immunocomplex was then split off from the carrier by adding 0.5 ml of 20 mM DTT in 0.1 M Na-phosphate buffer, pH 7.5–0.3 M NaCl (reaction for 3 h at room temperature whilst stirring). After centrifuging the product, 200 μl of the supernatant were removed and the radioactivity released measured.

A measuring result of 28149 cpm was obtained when measuring on Sephadex ®-conjugate prior to splitting off the $^{125}$I-containing immunocomplex and 6248 cpm (in 200 μl supernatant) subsequent to said splitting of the immunocomplex, which means that 78% of the activity was transferred in the liquid phase by splitting.

EXAMPLE 7

Assay of human γ-globulin with sheep-antihumanIgG-antibody-α-amylasemulticomplex conjugate (a) Preparation of sheep-antihumanIgG-antibody-α-amylasemulticomplex conjugate 30 mg of α-amylase (same type and pretreatment as in Example 1) were dissolved in 4.5 ml 0.1 M Na-phosphate-0.3 M NaCl pH 7.5. 100 μl 50 mM N-succinimidyl-3(2-pyridyldithio)propionate in abs. EtOH were added in portions of 25 μl at 5 minutes intervals. After 40 minutes at +25° C. the reaction mixture was gel filtered on Sephadex ® G-25 (the medium used was 0.1 M Na-phosphate-0.3 M NaCl pH 7.5), surplus reactant and low molecular reaction products being removed. The void material containing modified α-amylase (2-pyridyl-disulphide-α-amylase) was pooled to 8 ml. The substitution degree with respect to the content of 2-pyridyl disulphide groups was found to be 3.7 μmole 2-pyridyl disulphide groups/50 mg of α-amylase.

Another 2-pyridyl disulphide-α-amylase derivative was prepared as described above but with the difference that 400 μl 50 mM N-succinimidyl-3(2-pyridyldithio)propionate in abs. EtOH were added in portions of 100 μl at 5 minutes intervals. The degree of substitution of this derivative was found to be 7.5 μmole 2-pyridyl disulphide groups/50 mg of α-amylase.

2.5 mg of 2-pyridyl-disulphide-α-amylase containing 3.7 μmole 2-pyridyldisulphide groups/50 mg of α-amylase in 0.75 ml 0.1 M Na-phosphate-0.3 M NaCl pH 7.5 were mixed with 50 μl 50 mM dithiothreitol and reduced for 10 minutes at +25° C. Surplus dithiothreitol and low molecular reaction products were removed by gel filtration on Sephadex ® G-25 (the medium used was 0.3 M NaCl).

The void, 2.5 ml containing 2.3 mg thiol-α-amylase, was mixed with 1.5 mg of 2-pyridyl-disulphide-α-amylase containing 7.5 μmole 2-pyridyl disulphide groups/50 mg in 0.75 ml 0.1 M Na-phosphate-0.3 M NaCl. After reaction for 60 minutes at +25° C. the reaction was cut off by the addition of 50 μl 20 mM 2.2'-dipyridyl disulphide in abs. EtOH. 1 drop of Tween 20 was added and the mixture was chromatographed on a column of Sepharose ® 6B (80 ml total volume) (the medium used was 0.3 M NaCl-0.5% Tween 20). The void material (about 15 ml) containing about 0.19 mg α-amylase aggregate/ml containing 2.4 μmole 2-pyridyl disulphide groups was pooled and stored at +4° C.

6 mg of sheep-antihumanIgG-antibodies (immunosorbent-purified with γ-globulin-agarose sorbent prepared by coupling human electrophoretically purified γ-globulin to CNBr-activated Sepharose ® 4B (from Pharmacia Fine Chemicals AB, Uppsala, Sweden)) in 2.4 ml 0.1 M Na-phosphate-0.3 M NaCl pH 6.0 were mixed with 20 μl 50 mM N-succinimidyl-3(2-pyridyldithio)propionate in abs. EtOH. After 20 minutes at +25° C. surplus reactant was removed by gel filtration of the reaction mixture on Sephadex ® G-25 (the medium used was 0.1 M Na-acetate-0.3 M NaCl, pH 5.0). The void, about 3.0 ml, containing about 5.5 mg 2-pyridyl disulphide antibodies was pooled and reacted with 0.2 ml 50 mM dithiothreitol in distilled H$_2$O. After reaction for 25 minutes surplus dithiothreitol was removed by gel filtration of the reaction mixture on Sephadex$^{(R)}$ G-25 (the medium used was 0.3

M NaCl). The void, 5.0 ml, containing about 5 mg modified antibodies with a degree of substitution of about 2 μmole SH-groups per 160 mg of protein, was pooled.

About 0.2 mg of the antibodies thus thiolated in 0.2 ml 0.3 M NaCl was mixed with 0.4 mg of the α-amylase aggregate (vide above) in 2.0 ml 0.1 M Na-phosphate-0.3 M NaCl-0.5% Tween 20. The reaction mixture containing sheep-antihumanIgG-antibody-α-amylase multicomplex conjugate was stored at +4° C.

(b) Assay of human γ-globulin using sheep-antihumanIgG-antibody-α-amylase multicomplex conjugate About 50 ug (dried derivative) of agarose-sheep-antihumanIgG-antibody derivative (prepared by coupling immunosorbent purified sheep-antihumanIgG-antibodies to CNBr-activated Sepharose ® 4B) containing about 400 ng antibodies and suspended in 300 μl 0.3 M NaCl-0.5% Tween 20 are added to each tube in a series of polystyrene tubes (3 ml) containing varying amounts (1–500 ng) of human γ-globulin dissolved in 100 μl 0.1 M Na-phosphate-0.3 M NaCl-0.5% Tween 20, pH 7.4. A number of tubes containing only buffer and a number of tubes containing aminoethyl-agarose (prepared by coupling ethanolamine to CNBr-activated Sepharose ® 4B) were used as blanks.

The tubes were incubated for about 18 hours at +25° C. while being shaken carefully. The agarose gel of each tube was then washed by a repeated centrifuging-decanting procedure with 6×2 ml 0.3 M NaCl-0.5% Tween.

After the last washing, the supernatant was sucked off to 0.3 ml and 100 μl of the reaction mixture from Example 7 a) above containing sheep-antihumanIgG-antibody-α-amylase-multicomplex conjugate (about 400 ng with respect to antibodies) were added to each tube which then was incubated during careful shaking for 4 hours at +25° C. The solid material of each tube was washed again as described above with 6×2 ml 0.3 M NaCl-0.5% Tween 20.

1.0 ml 10 mM dithiothreitol in 0.1 M Na-phosphate-0.3 M NaCl pH 8 was added to the tubes (0.3 ml suspension). After reduction for 60 minutes (during which the α-amylase-multicomplex was set free from the immobilized immunocomplex and was split into smaller units) 1.0 ml of a suspension of Phadabas ® anaylase test (1 tablet/4 ml. Pharmacia Diagnostics AB, Uppsala, Sweden) was added and the tubes were incubated again for 60 minutes at +25° C. whereafter the reaction was cut off by the addition of 0.5 ml 0.5 M NaOH. After removing undissolved starch polymer by filtration, the extinction of the blue-coloured filtrate was determined by 620 nm. The extinction values are related to the α-amylase activity set free which is related to the amount of bound conjugate which in turn is related to the amount of bound γ-globulin and thus is a measure of the γ-globulin concentrations of the test solutions. Human γ-globulin could be detected down to a concentration of <1 ng/ml in this way.

EXAMPLE 8

Assay of human gammaglobulin with sheep-antihumanIgG-antibody-β-galactosidase conjugate

(a) Preparation of sheep-antihumanIgG-antibody-β-galactosidase conjugate

20 μl 8 mM N-succinimidyl-3(2-pyridyldithio)propionate (in 99.5% EtOH) was slowly added to 2 mg of sheep-antihumanIgG-anti-bodies (immunosorbent purified with agarose-human gammaglobulin sorbent prepared by coupling human electrophoretically purified gammaglobulin to CNBr-activated Sepharose ® 4B (from Pharmacia Fine Chemicals, AB, Uppsala, Sweden) in 0.6 ml 0.1 M Na-phosphate-1 mM MgCl$_2$, pH 7.0, while stirring for 60 minutes at +25° C. The reaction mixture is then gel filtered on a column of Sephadex$^{(R)}$G-25 (beads of dextran cross-linked with epichlorohydrin from Pharmacia Fine Chemicals AB, Uppsala, Sweden) (the medium used was the same phosphate buffer as the one mentioned above) and the void material (1.5 ml) containing about 1.8 mg of 2-pyridyl disulphide substituted antibodies was pooled.

1.3 mg of β-galactosidase (from Boehringer Mannheim GmbH, West Germany) in 0.5 ml 0.1 M Na-phosphate-1 mM MgCl$_2$, pH 7.0 were gel filtered on a column of Sephadex G-25. The void material, about 1.2 mg in 1.5 ml. was mixed with 1.8 mg 2-pyridyl disulphide-containing antibodies (vide above) in 1.5 ml 0.1 M Na-phosphate-1 mM MgCl$_2$. The reaction was then allowed to take place at +4° C. for about 48 hours, whereafter the reaction mixture was gel filtered on a column of Sepharose ® 6B (from Pharmacia Fine Chemicals AB) (the medium used was 0.3 M NaCl). The fractions containing β-galactosidase-antibody oligomers having a molecular weight of 650 000–800000 were pooled. The material thus pooled was stored at +4° C.

(b) Assay of human gammaglobulin with sheep-antihumanIgG-antibody-β-galactosidase conjugate The assay was carried out using so-called sandwich technique. 50 μl of a suspension of an agarose-sheep-antihumanIgG-antibody derivative (prepared by coupling immunosorbent purified sheep-antihumanIgG-antibodies to CNBr-activated Sepharose ® 4B) containing about 0.45 mg antibodies/ml suspension were added to each of a series of test tubes with varying amounts of human gammaglobulin (0.1–250 ng) dissolved in 100 μl 0.1 M Na-phosphate-0.3 M NaCl-0.5% Tween 20, pH 7.5. A number of tubes with only buffer and a number of tubes containing aminoethyl agarose (prepared by coupling ethanolamine to CNBr-activated Sepharose ® 4B) were used as blanks. The tubes were incubated for 18 hours at +25° C. while being shaken carefully. The agarose gel of each tube was then washed as described in Example 7.

20 μl 0.3 M NaCl containing sheep-antihumanIgG-antibody-β-galactosidase conjugate (the oligomeric conjugate prepared as above) were added to each tube containing the washed agarose suspensions (about 0.3 ml/tube). The tubes were then incubated for 4 hours at +25° C. while being shaken carefully. The agarose gel of each tube was then washed as described in Example 7. 0.1 ml 1 M β-mercaptoethanol was then added to each agarose suspension. Reduction was allowed to take place for 30 minutes at +25° C. This reduction resulted in the liberating of the β-galactosidase in native form from the immunocomplex immobilized on the agarose derivative.

0.2 ml o-nitrophenyl-β-D-galactoside (10.5 mg/ml) in 0.1 M Na-phosphate-1 mM $MgCl_2$ pH 7.0 was then added and the liberated β-galactosidase activity determined by spectrophotometrical (at 420 nm) measurement of the amount of o-nitrophenolate formed per unit of time. Liberated β-galactosidase activity is proportional to the amount of bound conjugate which in turn is proportional to the amount of bound gammaglobulin and thus is a measure for the gammaglobulin concentrations of the test solutions. Human gammaglobulin could in this way be detected down to a concentration of −1 ng/ml.

EXAMPLE 9

Assay of dextran with a 2-pyridyl disulphide dextran derivative in a competitive system involving agarose-concanavalin 100 μl of settled agarose-concanavalin (Con A-Sepharose ® 4B, Pharmacia Fine Chemicals AB, Uppsala, Sweden) and 200 μl 0.1 M Na-phosphate-0.3 M NaCl pH 7.5 were added to each of 8 Ellerman tubes. 0.2 mg of 2-pyridyl disulphide dextran (prepared according to Example 4) in 50 μl distilled water was then added to each tube. The tubes were then incubated for 20 minutes at +25° C. whilst being stirred carefully, whereafter 100 μl 0.3 M NaCl-0.1 M Na-phosphate pH 7.5 containing different amounts of dextran (Dextran T-40, Pharmacia Fine Chemicals AB, Uppsala, Sweden) were added to 6 of the tubes. To the remaining two tubes only 100 μl of said buffer was added. The tubes were then incubated for 60 minutes at +25° C. whilst being shaken carefully and were then washed by repeated centrifugations and decantations with 3×2 ml of said buffer.

Then the suspensions of all tubes were diluted to a volume of 2 ml with said buffer. 0.1 ml 50 mM dithiothreitol was added and the tubes shaken for 10 minutes at +25° C. The agarose gel of each tube was then separated by centrifugation and the concentrations of 2-thiopyridone of the supernatants measured spectrophotometrically at 343 nm. The amount of liberated 2-thiopyridone is proportional to the amount of 2-pyridyl disulphide dextran bound to the agarose-concanavalin and thus inversely proportional to the concentration of dextran of the test solution. The dextran concentration could in this way be detected in a concentration range of from 0.03-100 mg/ml.

EXAMPLE 10

Assay of human gammaglobulin with $^{125}$I-labelled sheep-antihumanIgG-antibodies involving a splittable humanIgG-glass-derivative (a) Preparation of humanIgG-glass-derivative 50 mg Thiol glass (Corning CPG 550, Corning Glass Co., USA) were reduced in 5 ml 0.1 M Na-phosphate-0.3 M NaCl, pH 7.5 containing 30 mM dithiothreitol. The reduced glass was thoroughly washed with 0.1 M Na-phosphate-0.3 M NaCl and suspended in 1 ml of said buffer, whereafter 20 μl 1,2-3,4-diepoxybutane were added. After reaction for 60 minutes the glass beads were washed with 0.1 M Na-phosphate-0.3 M NaCl pH 7.5. The glass derivative thus obtained was then suspended in 0.5 ml 0.2 M sodium carbonate buffer pH 9.5 and 0.5 mg electrophoretically purified human IgG dissolved in 0.5 ml 0.2 M Na-carbonate buffer pH 9.5. The reaction mixture was carefully stirred for 18 hours at +25° C. whereafter 50 μl 10% ethanolamine (the pH-value was adjusted to 9.5 with HCl) were added in order to remove unreacted epoxy groups. After 120 minutes at +25° C. the glass derivative was washed with 0.1 M Na-phosphate-0.3 M NaCl pH 7.5. The glass beads were then suspended in 20 ml 0.1 M Na-phosphate-0.3 M NaCl pH 7.5 containing 0.5% Tween 20. Analysis showed that the antibody concentration was about 16 μg/ml suspension.

(b) Substitution of sheep-antihumanIgG-antibodies with iodine-125

A test tube of glass was placed in an ice bath. 45 μg of sheep-antihumanIgG-antibodies (immunosorbent purified with agarose-humanIgG derivative prepared by coupling electrophoretically purified humanIgG to BrCN-activated Sepharose ® 4B (Pharmacia Fine Chemicals AB, Uppsala, Sweden)) dissolved in 10 μl 0.3 M NaCl were added to the tube. 40 μl 0.2 M Na-phosphate buffer pH 7.0 (0.02% $NaN_3$), 100 μl chloramine-T (1.5 mM) and 0.7 μl $Na^{125}I$ (0.36 mCi) were added. The reaction was cut off after 2 minutes by the addition of 20 μl M $Na_2S_2O_3$ and 50 μl 0.1 M KI. The reaction mixture was chromatographed on a column of Sephadex G-25 which was preprepared with 1 ml 1% bovine serum albumin and equilibrated with 0.05 M Na-phosphate buffer pH 7.4 containing 0.05% Tween 20, 0.02% $NaN_3$ and 0.05 M $Na_2S_2O_3$. The void fractions were pooled and diluted 5 times with 0.05 M Na-phosphate pH 7.0. Analysis showed that the pool (10 ml) contained ~4 μg labelled sheep-antihumanIgG-antibodies per ml.

(c) Assay of human gammaglobulin with $^{125}$I-labelled sheep-antihumanIgG-antibodies in a competitive system involving a splittable humanIgG-glass-derivative A series of Ellerman tubes containing respectively glass-humanIgG (100 μl suspension according to the above) and $^{125}$I-substituted sheep-antihuman IgG-antibodies (100 μl of a solution obtained by diluting the above mentioned solution 10 times in 0.1 M Na-phosphate-0.3 M NaCl-0.5% Tween 20, pH 7.5) was prepared. Then varying amounts of human gammaglobulin dissolved in 100 μl 0.1 M Na-phosphate-0.3 M NaCl-0.5% Tween 20, pH 7.5 were added to the tubes. The tubes were shaken for 4 hours at +25° C. on a shaking-table whereafter the glass beads were washed with 4×2 ml 0.1 M Na-phosphate-0.3 M NaCl—0.5% Tween 20, pH 7.5. The glass beads were then suspended in 0.5 ml of said phosphate buffer containing 20 mM sodium periodate. The vicinal diol structure which binds the human IgG to the glass is split hereby and the immunocomplex (human IgG-($^{125}$I-sheep-antihumanIgG-antibody-complex) enters into the solution. The reaction was allowed to take place for 60 minutes at +25° C. on a shaking-table whereafter liberated radioactivity in the supernatant was measured with a gamma counter. The amount of liberated radioactivity is proportional to the amount of $^{125}$I-labelled sheep-antihumanIgG-antibodies bound to the glass derivative and thus inversely proportional to the concentration of gammaglobulin of the test solutions.

The background effect due to unspecific uptake of $^{125}$I-labelled antibodies to the glass beads could be reduced by this process.

EXAMPLE 11

Assay of soya bean trypsin inhibitor with 2-pyridyl disulphide substituted soya bean trypsin inhibitor in a competitive system involving agarose-trypsin (a) Preparation of agarose-trypsin derivative 20 mg of trypsin (lyophilized trypsin, Worthington Biochem. Corp., USA) were mixed with a suspension of 2 g (dry-sucked) CNBr-activated Sepharose ® 4B (cyanogenbromide-activated agarose from Pharmacia Fine Chemicals AB, Uppsala, Sweden) in 2 ml 0.1 M NaHCO$_3$. The reaction mixture was stirred at +4° C. for 24 hours. The gel derivative formed was then washed with 0.1 M Na-phosphate-0.3 M NaCl, pH 7.5 (200 ml), 0.1 M Na-acetate-0.3 M NaCl pH 4.0 (200 ml), 0.1 M NaHCO$_3$-10 mM ethanolamine (200 ml) and finally with 0.1 M Na-phosphate-0.3 M NaCl pH 7.5 (200 ml). The gel was stored suspended in the last-mentioned solution at +4° C.

(b) Preparation of soya bean trypsin inhibitor 2-pyridyl disulphide derivative 18 mg soya bean trypsin inhibitor (trypsin inhibitor Type I-S: Lyophilized, Sigma Chem. Corp., USA) were dissolved in 0.1 ml 0.1 M Na-phosphate-0.3 M NaCl pH 7.5. The solution was gel filtered on a column of Sephadex ® G-25 (the medium used was the above buffer). 150 μl 50 mM N-succinimidyl-3(2-pyridyldithio)propionate were added in portions of 50 μl every fifth minute to the void material (2.0 ml containing about 16 mg protein). After reaction for 30 minutes at +25° C. the reaction mixture was gel filtered on a column of Sephadex ® G-25 (the medium used was 0.1 M Na-phosphate-0.3 M NaCl, pH 7.5). The void material, 3.0 ml, which contained soya bean trypsin inhibitor-2-pyridyl disulphide derivative 4.8 mg/ml with a degree of substitution of 4.3 μmole 2-pyridyl disulphide groups/20 mg protein was stored at +4° C.

(c) Assay of soya bean trypsin inhibitor with 2-pyridyl disulphide-substituted soya bean trypsin inhibitor The assay was carried out with so-called competitive technique. 100 mg of dry-sucked agarose-trypsin derivative (corresponding to about 1 mg trypsin) (vide above) and 1.4 mg of soya bean trypsin inhibitor-2-pyridyl-disulphide derivative in 0.3 ml 0.1 M Na-phosphate-0.3 M NaCl pH 7.5 (vide above) were added to each tube in a series of test tubes. Then 0.3 ml of soya bean trypsin inhibitor solutions of varying concentrations were added to the tubes, whereafter the tubes were shaken carefully for 60 minutes at +25° C. The agarose gel was then washed with 0.1 M Na-phosphate-0.3 M NaCl pH 7.5 and suspended in 2 ml of said buffer whereafter 0.2 ml 50 mM dithiothreitol was added. After shaking of the tubes for 10 minutes at +25° C., the agarose gel of each tube was separated by means of centrifugation and the amount of liberated 2-thiopyridone of the supernatants measured spectrophotometrically at 343 nm. The amount of liberated 2-thiopyridine is proportional to the amount of soya bean trypsin inhibitor 2-pyridyl disulphide derivative bound to the agarose-trypsin derivative and thus inversely proportional to the concentrations of native soya bean trypsin inhibitor of the test solutions. Solutions containing about 0.1–10 mg soya bean trypsin inhibitor/ml were used in the test.

EXAMPLE 12

Assay of human gammaglobulin with a sheep-antihumanIgG-antibody-dextran-α-amylase conjugate in a sandwich procedure involving dextranase for liberation of α-amylase from the immobilized immunocomplex (a) Preparation of sheep-antihumanIgG-antibody-dextran-α-amylase conjugate 13 mg α-amylase (vide Example 1) were dissolved in 1.1 ml 0.05 M Na-phosphate buffer-0.3 M NaCl, pH 7.5 and 110 μl 5 mM N-succinimidyl-3(2-pyridyldithio)propionate (in 99.5% EtOH) were added. The solution was shaken vigorously and then allowed to stand for 15 minutes, whereafter 100 μl 50 mM dithiothretiol were added. After additional 15 minutes the reaction mixture was gel filtered on a column of Sepharose ® G-25 (Pharmacia Fine Chemicals AB, Uppsala, Sweden) (the medium used was 0.3 M NaCl). The void material, 2.5 ml containing 4.70 mg of thiolated α-amylase/ml having a substitution degree of 0.9 mole HS-groups/mole protein, was collected.

The α-amylase thus thiolated (about 12 mg in 2.5 ml) was mixed with 12 mg of 2-pyridyl disulphide dextran (prepared according to Example 4) dissolved in 1.5 ml 0.1 M Na-phosphate-0.3 M NaCl, pH 7.5. The reaction was allowed to take place at +25° C. for 24 hours while stirring carefully, a dextran-α-amylase derivative being formed.

0.8 mg sheep-antihumanIgG-antibodies (immunosorbent purified as in Example 10 b)) in 0.3 ml 0.1 M Na-phosphate-0.3 M NaCl, pH 7.5, were mixed with 25 μl 5 mM N-succinimidyl-3(2-pyridyldithio)propionate in abs. ethanol. The reaction was allowed to take place at +25° C. whereafter the reaction mixture was gel filtered on a column of Sepharose ® G-25 (the medium used was 0.1 M Na-acetate pH 5.0). The void material, 0.7 mg in 0.7 ml. was reduced with 5 mM dithiothreitol for 30 minutes, whereafter surplus reducing agent was removed by another gel filtration on Sephadex ® G-25 (the medium used was 0.3 M NaCl). The thiolated antibodies thus obtained (the void material, 0.55 mg protein (1.0 ml) containing 2 mole HS/mole protein) were mixed with 0.1 ml of dextran-α-amylase derivative (vide above) and reaction was allowed to take place at +4° C. for 24 hours while stirring. The reaction mixture containing sheep-antihumanIgG-antibody-dextran-α-amylase conjugate was stored at +4° C.

(b) Assay of human gammaglobulin with sheep-antihumanIgG-antibody-dextran-α-amylase conjugate in a sandwich process involving dextranase for liberation of α-amylase from the immobilized immunocomplex 100 μl of a suspension of an agarose-sheep-antihumanIgG-antibody derivative (prepared analogous to Example 7 b)) containing about 50 μg antibodies/ml suspension were added to each tube in a series of test tubes with varying amounts of human gammaglobulin (0.5–300 ng) dissolved in 100 μl 0.1 M Na-phosphate-0.3 M NaCl-0.5% Tween 20, pH 7.5. A number of tubes with buffer only and a number of tubes containing aminoethyl agarose (prepared as described in Example 7 b)) served as blanks. The tubes were incubated for 18 hours at +25° C. while shaking carefully. The agarose gel of each tube was then washed as described in Example 7 b). 100 μl of a 100 times dilution of the reaction mixture containing sheep-antihumanIgG-antibody-dextran-α-amylase conjugate (vide above) were added to each tube contained the washed agarose suspensions (about 0.3 ml/tube). The tubes were then incubated for 18 hours at +25° C. while being shaken carefully, whereafter the agarose gel of each tube was washed as described in Example 7 b). 1.0 ml dextranase (DEX 0.5 mg/ml. Worthington Biochemical Corp., USA) in 0.1 M Na-phosphate-0.3 M NaCl, pH 7.5, was then added to all the tubes which were then incubated for 60 minutes at +25° C. The dextranase degrades the carrier dextran, α-amylase being liberated from the conjugate and the immobilized immunocomplex and entering into the solution. The liberated α-amylase activity was then determined as described in Example 7 b).

Liberated α-amylase activity is proportional to the amount of antibody-dextran-α-amylase conjugate bound to the agarose-immunocomplex derivative which amount in turn is proportional to the amount of gamma-globulin bound to the agarose-antibody derivative and thus is a measure for the concentrations of gamma-globulin of the test solutions. Human gammaglobulin could in this way be detected down to a concentration of about 1 ng/ml.

What is claimed is:

1. In the known method of carrying out assaying methods involving biospecific affinity reactions, in which there is used a component (I) which is labelled with at least one analytically indicatable group and is soluble in the liquid in whose presence the biospecific affinity reaction is carried out, for reaction with a counterpart (II) which exhibits biospecific affinity to (I) or with said counterpart (II) and also one or more additional counterparts exhibiting biospecific affinity to at least one of (I) and (II) and forming an insoluble conjugate in which the labelled component (I) is incorporated and which conjugate is separated from the liquid phase, whereafter the analytically indicatable group is assayed in the insoluble conjugate, the improvement which comprises (A)
  (a) using as the analytically indicatable group one which is bound to the component (I) with a splittable bond of covalent nature, or
  (b) using as one of said counterparts a counterpart which is bound to a carrier, which is insoluble in said liquid, with a splittable bond of covalent nature, or
  (c) using as the analytically indicatable group one which is bound to the component (I) with a splittable bond of covalent nature and using as one of said counterparts a counterpart which is bound to a carrier, which is insoluble in said liquid, with a splittable bond of covalent nature, said splittable bonds, which can be the same or different, being splittable under conditions which have practically no disturbing influence on the assay method used; and (B) splitting the insoluble conjugate at said splittable bond or bonds, in the presence of a liquid, to form fragments which are soluble in said liquid and which contain the analytically indicatable group, which group is then assayed in the liquid phase.

2. A method according to claim 1, wherein said biospecific affinity reaction is an immunochemical reaction.

3. A method according to claim 1 wherein said component (I) is an immunochemical component (I).

4. A method according to claim 1, wherein said counterpart (II) is an immunochemical counterpart (II).

5. A method according to claim 1 wherein an immunochemical counterpart is involved as said at least one additional counterparts.

6. A method according to claim 1 wherein the analytically indicatable group is an enzymatically active group.

7. A method according to claim 1 wherein the analytically indicatable group is an enzymatically active group or a fluroescent group, said group comprising the only part of the conjugate being bound with the splittable bond.

8. A method according to claim 1, or 5, or 6, wherein the splittable bond is a disulphide bond —S—S—.

9. A method according to claim 1, or 5, or 6, wherein the splittable bond is an enzymatically splittable bond.

10. In the known method of carrying out assaying methods involving biospecific affinity reactions, in which there is used a component (I), which is labelled with at least one analytically indicatable group and is soluble in the liquid in whose presence the biospecific affinity reaction is carried out, for reaction with a counterpart (II) which exhibits biospecific affinity to (I) or with said counterpart (II) and also one or more additional counterparts exhibiting biospecific affinity to at least one of (I) and (II) and forming an insoluble conjugate in which the labelled component (I) is incorporated and which conjugate is separated from the liquid phase, whereafter the analytically indicatable group is assayed in the insoluble conjugate, the improvement which comprises (A)
  (a) using as the analytically indicatable group one which is bound to the component (I) with a splittable bond of covalent nature, or
  (b) using as one of said counterparts a counterpart which is bound to a carrier, which is insoluble in said liquid, with a splittable bond of covalent nature, or
  (c) as the analytically indicatable group one which is bound to the component (I) with a splittable bond of covalent nature and as one of said counterparts a counterpart which is bound to a carrier which is insoluble in said liquid, with a splittable bond of covalent nature,
  said splittable bonds, which can be the same or different, being splittable under conditions which have practically no disturbing influence on the assay method used and said labelled component (I) comprising a multi-conjugate of a plurality of analytically indicatable groups linked together via linkages containing splittable bonds, said multiconjugate of indicatable groups in turn being bound to the component (I); and (B) splitting the insoluble conjugate at said splittable bond or bonds, in the presence of a liquid, to form fragments which are soluble in said liquid and which contain the analytically indicatable group, which group is then assayed in the liquid phase.

11. A method according to claim 10 wherein said biospecific affinity reaction is an immunochemical reaction.

12. A method according to claim 10 wherein said component (I) is an immunochemical component (I).

13. A method according to claim 10 wherein said counterpart (II) is an immunochemical counterpart (II).

14. A method according to claim 10 wherein an immunochemical counterpart is involved as said at least one additional counterpart.

15. A method according to claim 10 wherein the analytically indicatable group is an enzymatically active group.

16. A method according to claim 10 wherein the analytically indicatable group is an enzymatically active group or a fluorescent group, said group comprising the only part of the conjugate being bound with the splittable bond.

17. A method according to claim 10, 15 or 16, wherein the splittable bond is a disulphate bond —S—S—.

18. A method according to claim 10, or 15, or 16 wherein the splittable bond is an enzymatically splittable bond.

19. A reagent for use in assaying methods involving biospecific affinity reactions which reagent comprises a labelled immunochemical component (I) comprising a multi-conjugate of a plurality of analytically indicatable groups linked together via linkages containing splittable covalent bonds, said multiconjugate of indicatable groups in turn being bound to the immunochemical component.

20. A reagent according to claim 19 wherein the splittable bond is a disulphide bond —S—S—.

* * * * *